US00RE35887E

United States Patent [19]

Ishii et al.

[11] E Patent Number: Re. 35,887

[45] Reissued Date of Patent: Sep. 8, 1998

[54] CONVERSION EFFICIENCY MEASURING APPARATUS OF CATALYST USED FOR EXHAUST GAS PURIFICATION OF INTERNAL COMBUSTION ENGINE AND THE METHOD OF THE SAME

[75] Inventors: Toshio Ishii, Mito; Masayoshi Kaneyasu, Hitachi; Seiji Asano, Hitachinaka, all of Japan

[73] Assignee: Hitachi, Ltd., Tokyo, Japan

[21] Appl. No.: 519,098

[22] Filed: Aug. 24, 1995

Related U.S. Patent Documents

Reissue of:

[64] Patent No.: 5,237,818
Issued: Aug. 24, 1993
Appl. No.: 854,390
Filed: Mar. 19, 1992

[30] Foreign Application Priority Data

Mar. 20, 1991 [JP] Japan ..... 3-57106

[51] Int. Cl.[6] ..... F01N 3/20

[52] U.S. Cl. ..... 60/274; 60/276; 60/277; 60/285; 73/118.1; 123/691

[58] Field of Search ..... 60/274, 276, 277, 60/285; 73/118.1; 123/691

[56] References Cited

U.S. PATENT DOCUMENTS

| | | | |
|---|---|---|---|
| 3,969,932 | 7/1976 | Rieger | 60/276 |
| 4,622,809 | 11/1986 | Abthoff | 60/276 |
| 5,154,055 | 10/1992 | Nakane | 60/276 |

*Primary Examiner*—Douglas Hart
*Attorney, Agent, or Firm*—Antonelli, Terry, Stout & Kraus, LLP

[57] ABSTRACT

A conversion efficiency of a catalyst is estimated by a correlation function concerning output signals of upper and down stream side air fuel ratio sensors. The conversion efficiency is measured by comparing the correlation function and a complementary value of the correlation function with a comparing standard value.

37 Claims, 8 Drawing Sheets

CONVERSION EFFICIENCY MEASURING APPARATUS OF CATALYST USED FOR EXHAUST GAS PURIFICATION OF INTERNAL COMBUSTION ENGINE AND THE METHOD OF THE SAME

Matter enclosed in heavy brackets [ ] appears in the original patent but forms no part of this reissue specification; matter printed in italics indicates the additions made by reissue.

FIELD OF THE INVENTION

The present invention relates to an apparatus and a method for discriminating degradation of a catalyst having a function of removing deleterious components included in an exhaust gas of an internal combustion engine. More specifically, the present invention relates to an apparatus and a method for discriminating the degradation of the catalyst in a system having air fuel ratio sensors located upstream and downstream sides of the catalyst, which is located in an exhaust gas passage of the internal combustion engine.

BACKGROUND OF THE INVENTION

A system having air fuel ratio sensors located at upstream and downstream sides of the catalyst located in an exhaust gas passage of the internal combustion engine, for example, is disclosed in Japanese Patent Laid-Open No. 2-190756 published on Jul. 26, 1990 and entitled "Method and Apparatus for detecting a state of a catalyst". The prior art discloses that the degradation of the catalyst is discriminated by a phase difference, between two $O_2$ sensors located at upstream and downstream sides of the catalyst used for an exhaust gas purification of an internal combustion engine and judged in such a manner that the catalyst is degraded when the phase difference reaches less than a predetermined value.

The prior art has a following drawback:

The sensor located at the downstream side of the catalyst is affected by electrical noises, for example, ignition noise, so that this sensor can not give accurate information of exhaust gases flowing through the sensor. Accordingly, the degradation of the catalyst can not be detected accurately only by means of the phase difference mentioned above.

SUMMARY OF THE INVENTION

An object of the present invention is to provide an apparatus and a method which are capable of discriminating accurately the degradation of the catalyst used for the exhaust gas purification of an internal combustion engine.

The object of the present invention is attained by calculating a correction function of outputs of air fuel ratio sensors provided at the upstream and downstream sides of the catalyst during an ordinary air fuel ratio feedback control period.

According to the present invention, the degradation cf the catalyst connected to an internal combustion engine can be discriminated without an actual air fuel ratio control being deviated from a set air fuel ratio control as apparent from an explanation mentioned later.

DETAILED DESCRIPTION OF THE PREFERRED EMBODIMENTS

Figure 1:
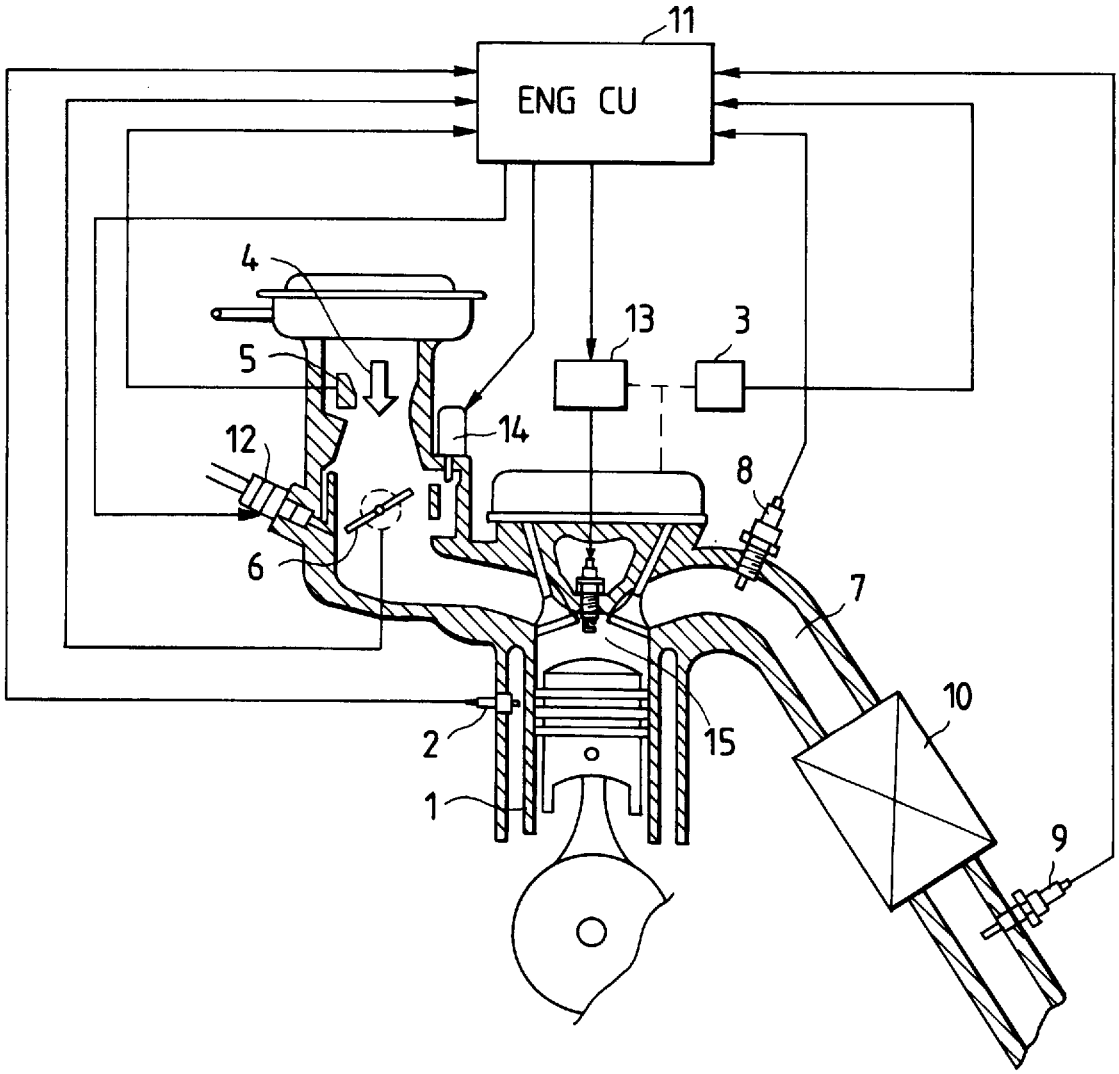
FIG. 1 illustrates a schematic diagram of a system applied to the present invention.

Referring to FIG. 1, an air flow amount 4 supplied to the internal combustion engine is measured by an air flow meter 5. Output signals from a sensor 2 for detecting the temperature of the internal combustion engine, a sensor for detecting a degree of opening of a throttle valve, the air flow meter 5 and a sensor 3 for detecting rotation of the engine are inputted to an engine control unit 11. The engine control unit 11 calculates a fuel injection amount and an ignition timing. A fuel injection valve 12 supplies the fuel to the engine according to the calculated fuel injection signal. An ignition device 13 outputs ignition signals to an ignition plug 15. The engine is cooled by cooling water 1. An idle speed control valve 14 is also controlled by a control signal from the engine control unit 11. A three way catalyst 10 converts harmful materials passing through an exhaust gas pipe 7 to harmless materials. An air fuel ratio sensor 8 is provided at an upstream side of the catalyst 10 and outputs a signal corresponding to an oxygen concentration of the exhaust gas. The fuel amount supplied to the engine is controlled by feeding back the output signal of the air fuel ratio sensor 8 so as to bring the air fuel ratio closer to a theoretical air fuel ratio. An air fuel ratio sensor 9 is provided at a downstream side of the catalyst 10 and detects the air fuel ratio thereat.

Figures 2A, 2B, 2C, 2D, 2E:
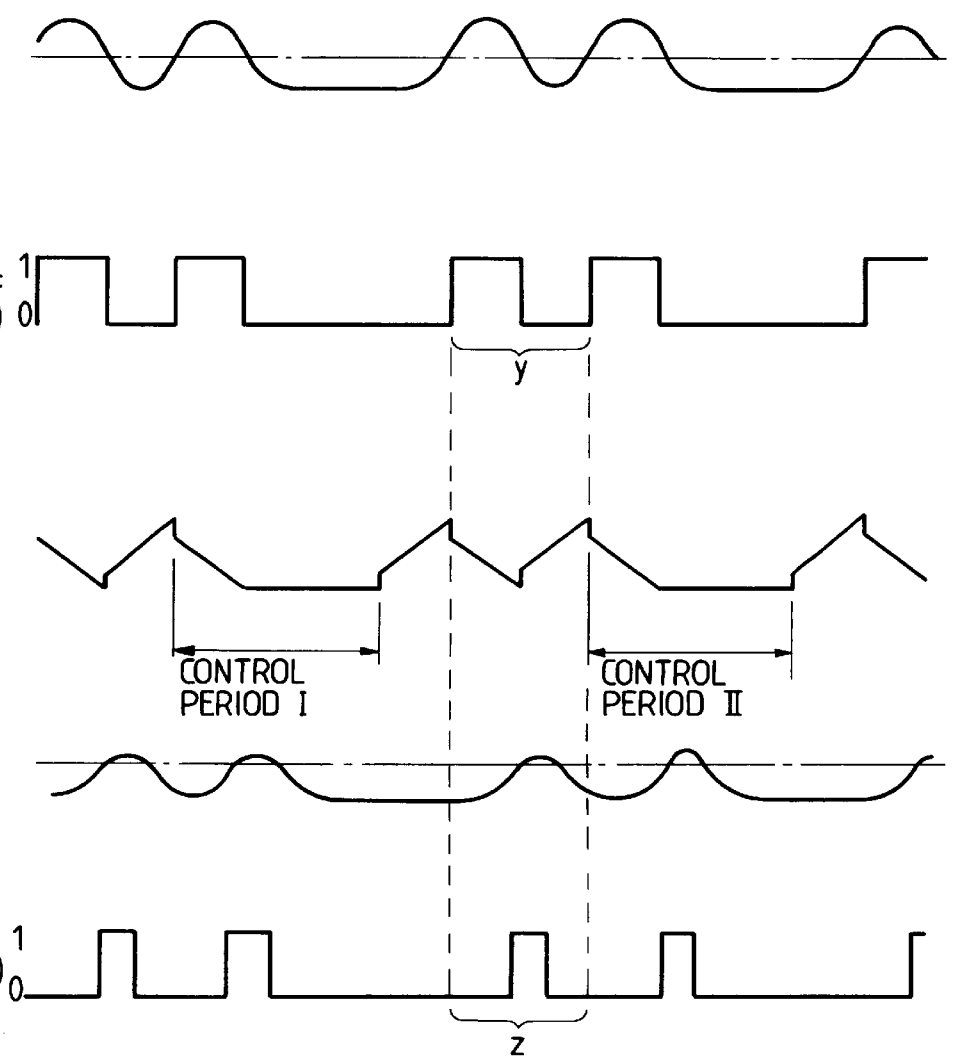
FIGS. 2(a), 2(b), 2(c), 2(d) and 2(e) show a diagram for explaining output signals produced within an engine control unit based on output signals of air fuel ratio sensors provided at upstream and downstream sides of a catalyst.

FIG. 2(a) shows a waveform of the air fuel ratio sensor 8 and a comparison level 1. A value of the comparison level 1 equals a mean value of the maximum and minimum values of the wave of the air fuel ratio sensor 8. FIG. 2(b) shows a binary code signal which is generated by comparing the output signal of the air fuel ratio sensor 8 with the comparison level 1 FIG. 2(c) shows a variation of a feedback coefficient of the air fuel ratio according to the output signal of the air fuel ratio sensor 8 shown in FIG. 2(a). FIG. 2(d) shows a waveform of the air fuel ratio sensor 9 and a comparison level 2. A value of the comparison level 2 is decided based on a characteristic of the air fuel ratio sensor 8 relating to the feedback control of the air fuel ratio sensor 9 relating to the feedback control of the air fuel ratio by the sensor 8. FIG. 2(e) shows a binary code signal which is generated by comparing the output signal of the air fuel ratio sensor 9 with the comparison level 2. Symbols y and z in FIGS. 2(b) and 2(d) denote an interval in which a correlation function is calculated. The region z containing the space where a rectangular wave is not generated is made to equal to a fixed interval of the feedback coefficient of the air fuel ratio. The correlation is calculated by y and z.

Figure 3:
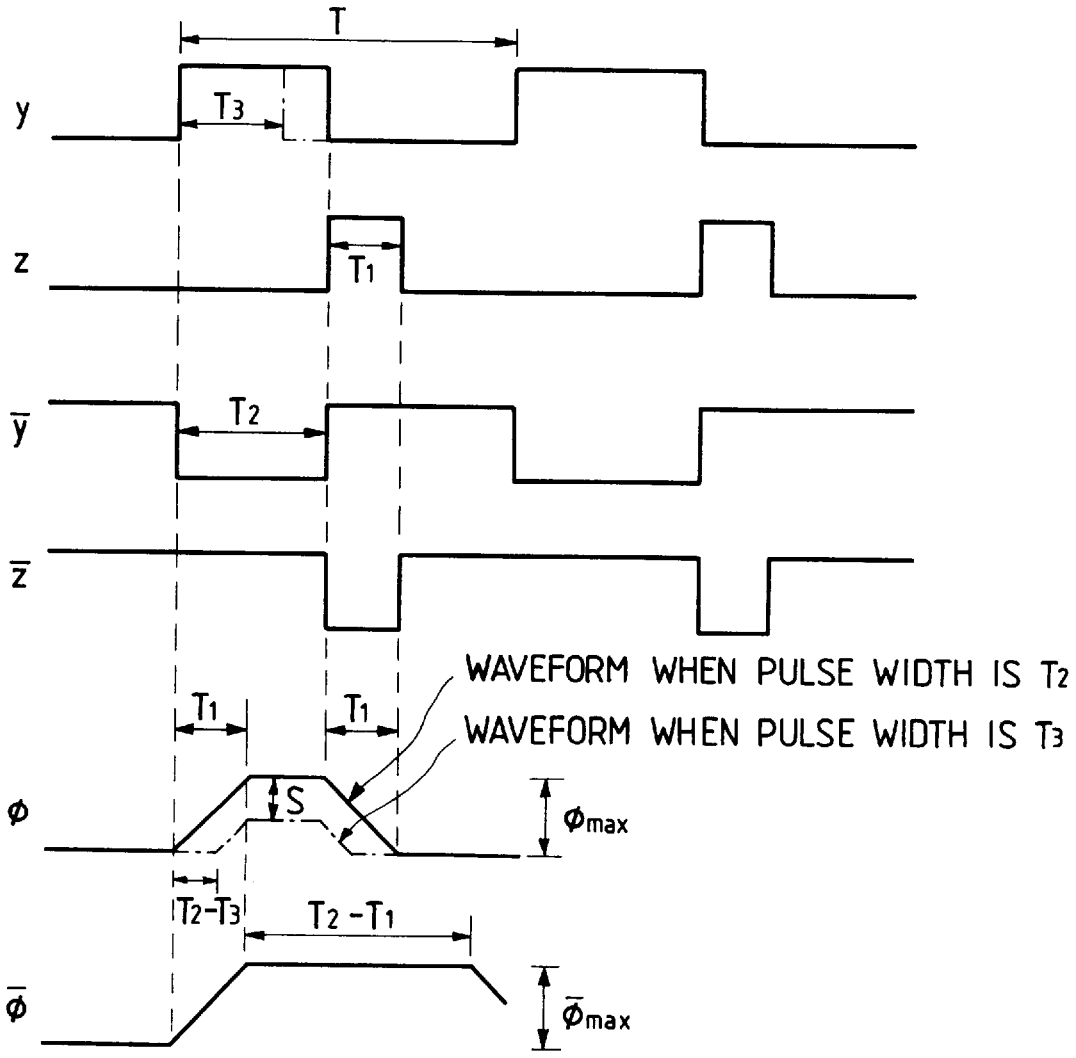
FIG. 3 shows a diagram for explaining calculation examples of a correlation function and a complement value of the correlation function which taken place in the present invention.

Referring to FIG. 3, symbols $\bar{y}$ and $\bar{z}$ denote complement signals of y and z, respectively.

The correlation function $\phi(\tau)$ is shown analogously as follows:

$$\phi(\tau) = \frac{\int_0^{\tau}\int_{-T}^{T} f_1(t)f_2(1-\tau)dtd\tau}{2T} \quad (1)$$

where, $f_1$ and $f_2$:function of time, such as the input and output of a communication system, $\tau$:time-delay parameter, and T:time interval.

In the present invention, the correlation function $\phi_j$ is calculated according to the following equation.

$$\phi_j = \sum_i y_i \cdot z_{i+j} \quad (2)$$

where, i:sampling number of y, and j:phase difference to i.

A complement function $\phi_j$ of the correlation function $\phi_j$ is shown as follows.

$$\phi_j = \sum_i y_1 \cdot z_{i+j} \quad (3)$$

In FIG. 3, waveforms of the correction function $\phi_j$ and the complement function $\phi_j$ of the correlation function $\phi_j$ are shown. The waveform of the correlation function $\phi_j$ and the complement function in FIG. 3 show ones which are calculated in one cycle T concerning y and $\bar{y}$, respectively.

The conversion efficiency CE of the catalyst is calculated by the following equation for compensating an effect of an output ratio between a high level output period and a low level output period of the upstream side air fuel ratio sensor 8.

$$CE \propto \phi_{max} + \phi_{max} \quad (4)$$

where, $\phi_{max} = \max(\phi_j)$

The conversion efficiency CE is calculated by the equation (4) in principle. However, the conversion efficiency CE is calculated by either $\phi_{max}$ or $\phi_{max}$. When the conversion efficiency CE is calculated based on $\phi_{max}$ or $\phi_{max}$, $\phi_{max}$ or $\phi_{max}$ has to be compensated by a duty ratio of y or $\bar{y}$ signal, respectively.

Figure 4:
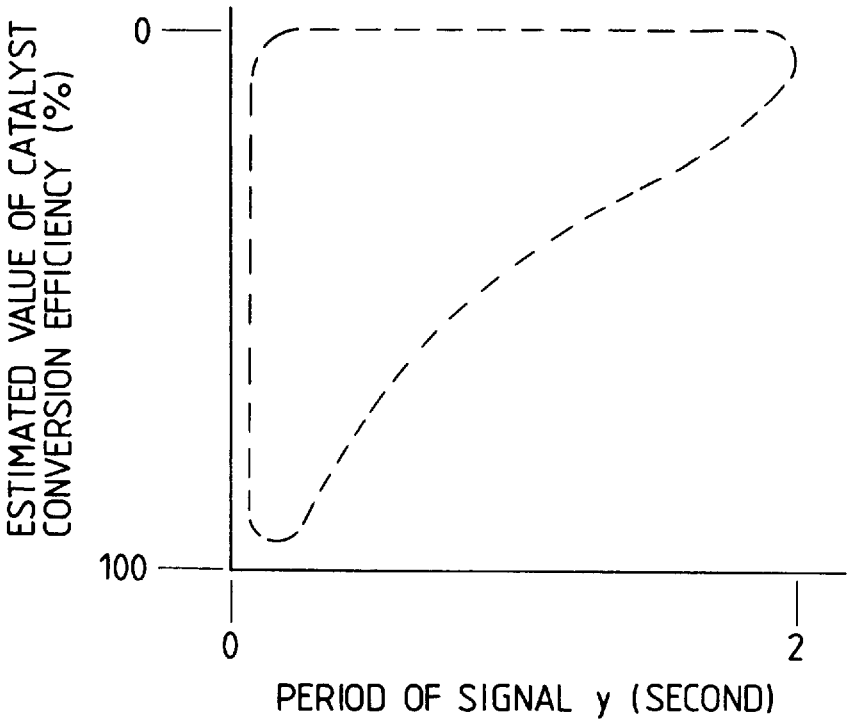
FIG. 4 shows a diagram of a characteristic between period of signal y shown in FIG. 3 and estimated value of catalyst conversion efficiency.

Referring to FIG. 4, the portion enclosed by a dotted line denotes a region in which the conversion efficiency of the catalyst can not be performed effectively and the harmful materials contained in the exhaust gas can not be converted perfectly. When the estimated conversion efficiency of the catalyst is in the region enclosed by the dotted line, a driver of a car or automobile is announced by an indicator such as a lamp.

Since the output of the air fuel ratio sensor 9 located at the downstream side of the catalyst 10 has a time delay against the output of the air fuel ratio sensor 8 located at the upstream side of the catalyst 10, an appropriate phase difference has to be prepared in a memory (not shown) in the engine control unit 11 as a phase difference between the output signal of the upstream side air fuel ratio sensor 8 and the downstream side air fuel ratio sensor 9. In the embodiment of the present invention, the above-mentioned phase difference is given between the output signal of the upstream side air fuel, ratio sensor 8 and the output signal of the downstream side air fuel ratio sensor 9 using a wash coat catalyst 10, and $\phi_{max}$ shown in FIG. 3 is measured. The duty ratio of the rectangular wave shown in FIG. 2(b) is approximately 50%, when a half period of the pulse width T of the signal y during 1 cycle thereof, in which the correlation is calculated, is $T_2$ as shown in FIG. 3. When the period $T_2$ is changed to $T_3$ in a system carrying out the feedback control by the upper stream side air fuel ratio sensor 8 on account of an error of the duty ratio of the signal y, the waveform of the correlation function $\phi_j$ has an estimated error S shown in FIG. 3. For preventing the estimated error of the conversion efficiency of the catalyst based on an error of the duty ratio of the signal y for calculating the correlation function, the coefficient CE shown by the equation (4) is calculated. The period of the signal y can be compensated by a ratio of $T_3$ to T as another compensation method of the duty ratio. The map shown in FIG. 4 can be also alternated depending on an engine state in case of the conversion efficiency of the catalyst being judged.

Figure 5:
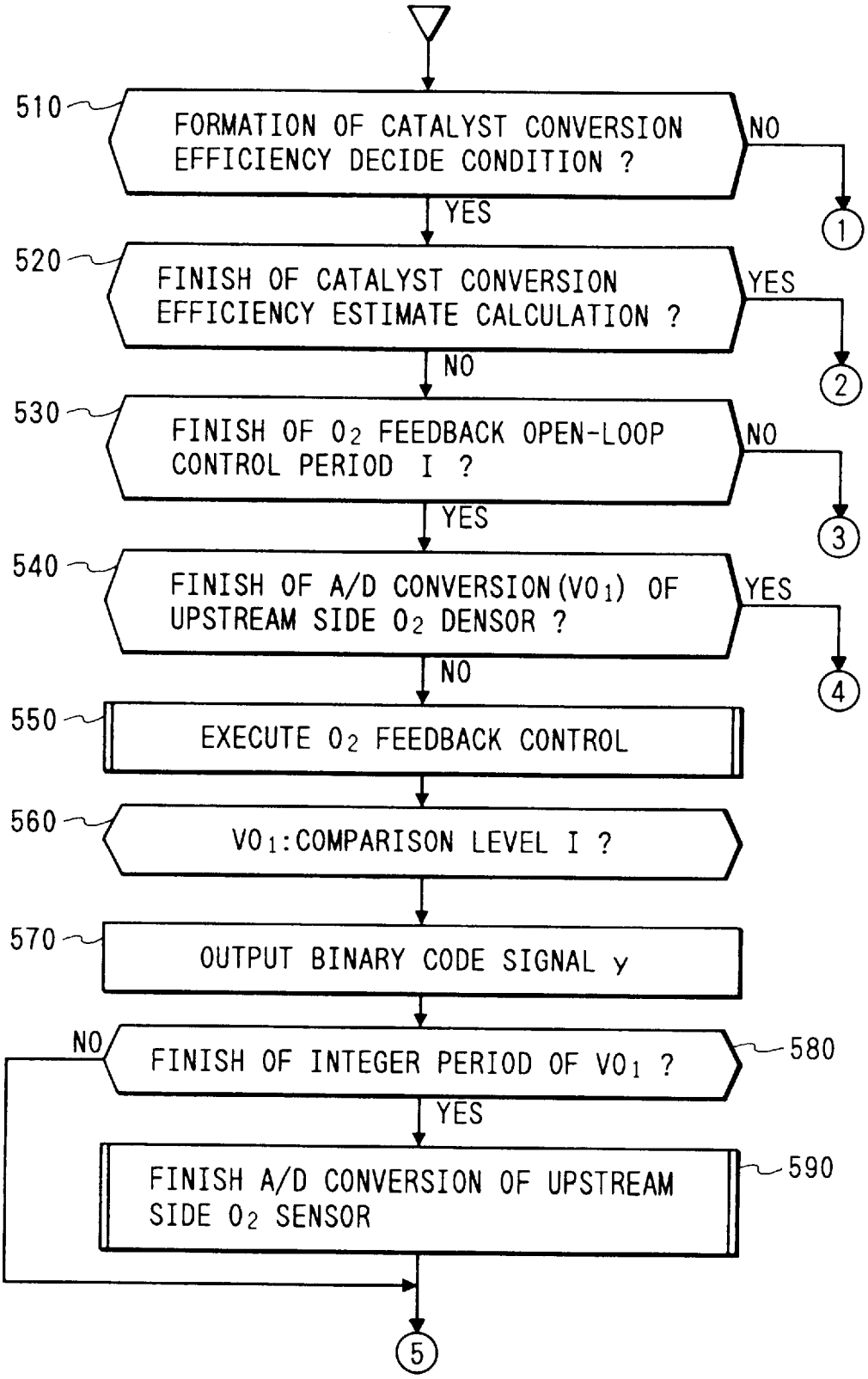
FIG. 5 shows a flow chart from step 510 to step 590 in one embodiment of the present invention.

Referring to FIG. 5, step 510 discriminates whether the present state is suitable for discriminating the conversion efficiency of the catalyst by elements of the engine driving condition, the catalyst temperature and proceeded time from the engine starting. Step 520 discriminates whether the estimating calculation CE of the conversion efficiency of the catalyst is finished. Step 530 discriminates whether the open loop control period I shown in FIG. 2C, which takes place before the feedback control of the air fuel ratio used for the calculation of the conversion efficiency of the catalyst is carried out, is finished. Step 540 discriminates whether the output of the air fuel ratio sensor provided at the upstream side of the catalyst and used for calculating the conversion efficiency of the catalyst is sampled for a predetermined period during the air fuel ratio feedback control. A usual air fuel ratio feedback control takes place at step 550. Step 560 discriminates whether the comparison level 1 is generated. The binary code signal y is generated by comparing the air fuel ratio sensor output at the upstream side of the catalyst with the comparison level 1 at step 570. Step 580 discriminates whether the comparison level 1 is generated for an integer period of at least one cycle of the signal y. Step 590 discriminates whether the feedback control of the air fuel ratio used for the estimate calculation of the conversion efficiency of the catalyst is finished.

Figure 6:
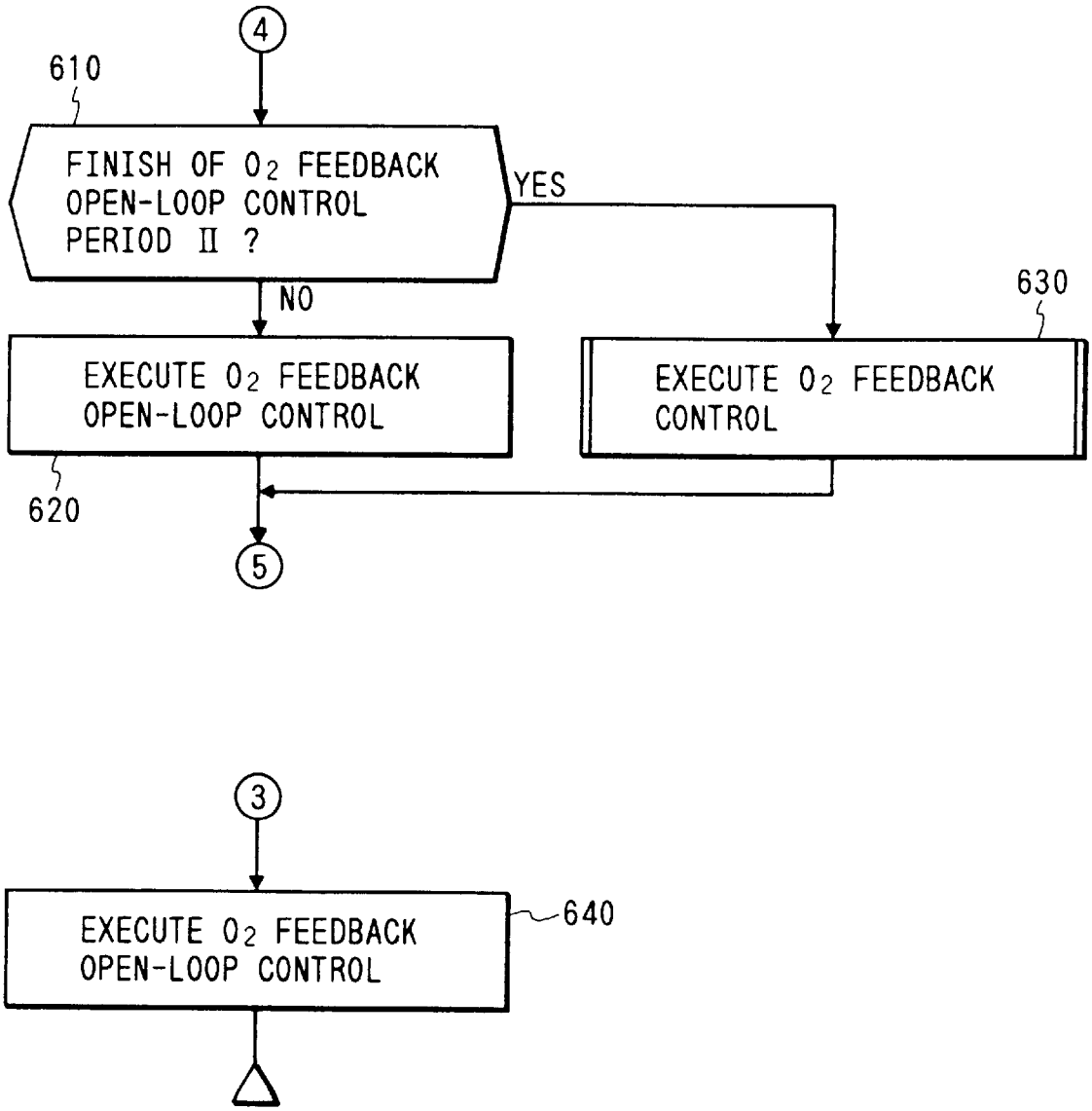
FIG. 6 shows a flow chart from step 610 to step 640 in one embodiment of the present invention.

Referring to FIG. 6, step 610 discriminates whether the open-loop control period II shown in FIG. 2C is finished after the air fuel ratio feedback control take place. The open-loop control periods I and II take place at step 620. A feedback control except the open-loop control periods I and II takes place at step 630. Step 640 selects the air fuel ratio open-loop control.

Figure 7:
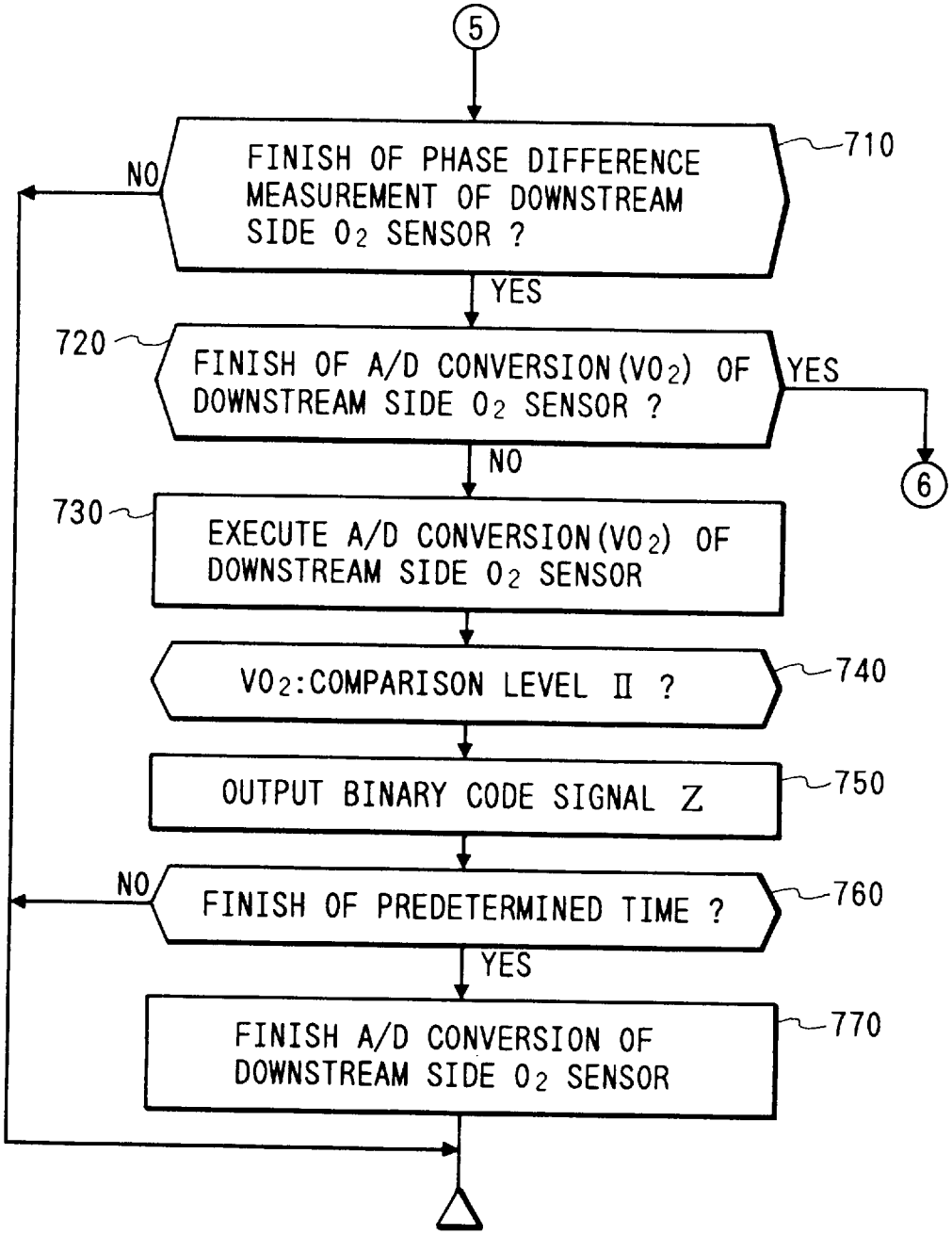
FIG. 7 shows a flow chart from step 710 to step 770 in one embodiment of the present invention.

Referring to FIG. 7, step 710 calculates the time delay corresponding to the phase difference between the upstream side air fuel ratio sensor and the downstream side air fuel ratio sensor. Step 720 discriminates whether the sampling period of the output of the downstream side air fuel ratio sensor used for the catalyst is finished. Step 730 carries out the sampling of the downstream side air fuel ratio sensor. Step 740 discriminates whether the comparison level 2 is generated. The binary code signal z is generated at step 750. Step 760 discriminates whether a predetermined time, for example, at least 1 cycle of the signal z is proceeded. Step 770 discriminates whether the sampling of the downstream side air fuel ratio output is finished.

Figure 8:
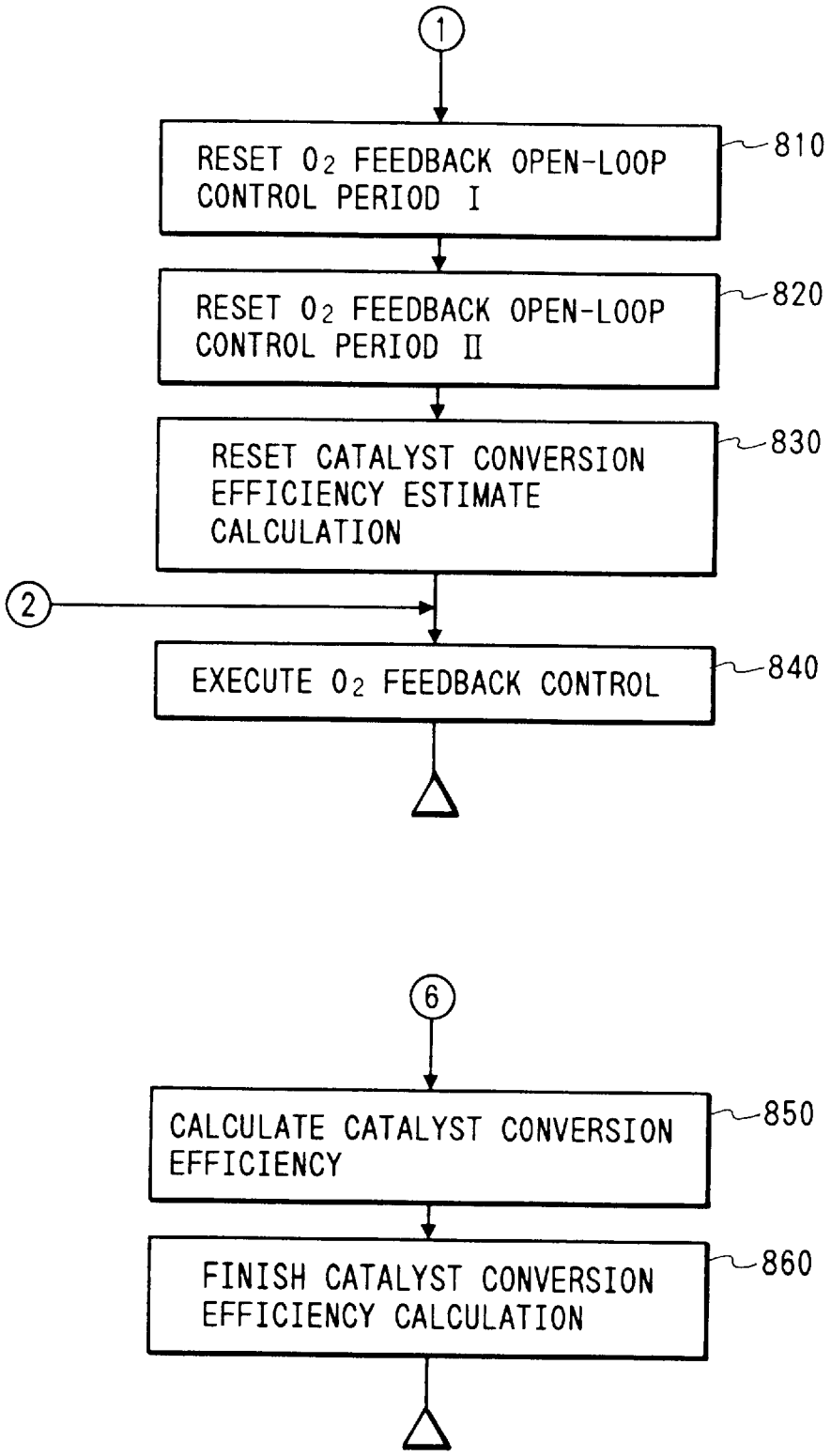
FIG. 8 shows a flow chart from step 810 to step 860 in one embodiment of the present invention.

Referring to FIG. 8, step 810 resets the air fuel ratio open-loop control period I and prepares for carrying out the estimated calculation of the conversion efficiency of the catalyst when the condition for calculating the conversion efficiency thereof is formed. Step 820 resets the air fuel ratio open-loop control period II and prepares for carrying out the estimated calculation as well as the step 810. Step 830 resets the estimated calculation of the conversion efficiency of the catalyst. An ordinal air fuel ratio feedback control takes place at step 840. At step 850, the estimated calculation of the conversion efficiency of the catalyst takes place. The estimated calculation of the conversion efficiency of the catalyst is finished at step 860.

Since the present invention judges the degradation of the catalyst at the exhaust gas passage in the internal combustion engine by measuring the similarity between the output change of the upstream side air fuel ratio sensor of the catalyst, namely the phase difference, the amplitude or the output waveform thereof, and the output change of the downstream side air fuel ratio sensor concerning the same frequency component of the upstream and downstream side air fuel ratio sensors in the form of the maximum amplitude of the calculated correlation function and comparing the maximum amplitude of the calculated correlation function with a reference value showing whether the catalyst is degraded, the present invention can measure accurately the degradation of the catalyst without causing a deviation between the actual air fuel ratio and the set air fuel ratio.

What we claim is:

1. A conversion efficiency measuring apparatus of a catalyst used for an exhaust gas purification of an internal combustion engine comprising a catalyst used for an exhaust gas purification provided at an exhaust gas passage of an internal combustion engine, gas component sensing means provided at an upstream side and a downstream side of said catalyst used for said exhaust gas purification, and means for calculating a correlation function based on an output signal from said exhaust gas component sensing means and estimating the conversion efficiency of said catalyst for said exhaust gas purification based on a signal generated by comparing a calculated value of the correlation function with a comparison level used for estimating the conversion efficiency of said catalyst used for said exhaust gas purification.

2. A conversion efficiency measuring apparatus of a catalyst used for an exhaust gas purification of an internal combustion engine according to claim 1, wherein further comprising a feedback control means of a fuel amount which is supplied to said internal combustion engine based on an output signal of the exhaust gas component sensing means provided at the upstream side of said catalyst used for said exhaust gas purification.

3. A conversion efficiency measuring apparatus of a catalyst used for an exhaust gas purification of an internal combustion engine according to claim 1, wherein further comprising a feedback control means of a fuel amount which is supplied to said internal combustion engine based on an output signal of the exhaust gas component sensing means provided at the downstream side of said catalyst used for said exhaust gas purification.

4. A conversion efficiency measuring apparatus of a catalyst used for an exhaust gas purification of an internal combustion engine according to claim 1, wherein said means for calculating said correlation function and estimating said conversion efficiency of said catalyst used for said exhaust gas purification calculates said correlation function based on a first rectangular wave signal which is generated by comparing an output signal from the exhaust gas component sensing means provided at said upstream side of said catalyst used for said exhaust gas purification with a first comparison level and a second rectangular wave signal which is generated by comparing another output signal from the exhaust gas component sensing means provided at said downstream side of said catalyst used for said exhaust gas purification with a second comparison level.

5. A conversion efficiency measuring apparatus of a catalyst used for an exhaust gas purification of an internal combustion engine according to claim 1, wherein said means for calculating said correlation function and measuring said conversion efficiency of said catalyst used for said exhaust gas purification outputs a signal which is generated by comparing a complement signal which is obtained by reversing said correlation function with a comparative level for estimating said conversion efficiency of said catalyst used for said exhaust gas purification.

6. A conversion efficiency measuring apparatus of a catalyst used for an exhaust gas purification of an internal combustion engine according to claim 1, wherein said means for calculating said correlation function and measuring said conversion efficiency of said catalyst used for said exhaust gas purification generates an output signal for estimating the conversion efficiency of said catalyst used for said exhaust gas purification by comparing at least one signal among an absolute value of said correlation function, a maximum value of said correlation function or a phase having the maximum value of said correlation function with a comparison level for estimating said conversion efficiency of said catalyst used for said exhaust gas purification

7. A conversion efficiency measuring apparatus of a catalyst used for an exhaust gas purification of an internal combustion engine according to claim 1, wherein said means for calculating said correlation function and measuring said conversion efficiency of said catalyst used for said exhaust gas purification calculates said correlation function within an interval of integral multiples of an air fuel ratio feedback control period.

8. A conversion efficiency measuring apparatus of a catalyst used for an exhaust gas purification of an internal combustion engine according to claim 1, wherein said means for calculating said correlation function and estimating said conversion efficiency of said catalyst used for said exhaust gas purification has an open-loop control period of the air fuel ratio before, after or before and after said correlation function being calculated.

9. A conversion efficiency measuring apparatus of a catalyst used for an exhaust gas purification of an internal combustion engine according to claim 1, wherein said means for calculating said correlation function and estimating said conversion efficiency of said catalyst used for said exhaust gas purification comprises a calculation means for calculating said correlation function, a memory means for memorizing a comparison level which is used for estimating the conversion efficiency of said catalyst used for said exhaust gas purification and a comparison means for comparing an output signal from said calculation means with an output signal from said memory means.

10. A conversion efficiency measuring apparatus of a catalyst used for an exhaust gas purification of an internal combustion engine according to claim 4, wherein said means for calculating said correlation function and estimating said conversion efficiency of said catalyst used for said exhaust gas purification measures said conversion efficiency of said catalyst used for said exhaust gas purification by comparing an output signal of said correlation function which is calculated based on said first rectangular wave signal and said second rectangular wave signal and another output signal of a correlation function which is calculated based on a complement signal of said first rectangular wave signal and another complemental signal of said second rectangular wave signal with a comparison level for estimating said conversion efficiency of said catalyst used for said exhaust gas purification.

11. A conversion efficiency measuring apparatus of a catalyst used for an exhaust gas purification of an internal combustion engine according to claim 4, wherein said means for calculating said correlation function and measuring said conversion efficiency of said catalyst used for said exhaust gas purification generates an output signal for estimating the conversion efficiency of said catalyst used for said exhaust gas purification by comparing at least one signal among an absolute value of said correlation function, a maximum value of said correlation function or a phase having the maximum value of said correlation function with a comparison level for estimating said conversion efficiency of said catalyst used for said exhaust gas purification.

12. A conversion efficiency measuring apparatus of a catalyst used for an exhaust gas purification of an internal combustion engine according to claim 4, wherein said means for calculating said correlation function and measuring said conversion efficiency of said catalyst used for said exhaust gas purification calculates said correlation function within an interval of integral multiples of an air fuel ratio feedback control period.

13. A conversion efficiency measuring apparatus of a catalyst used for an exhaust gas purification of an internal combustion engine according to claim 4, wherein said means for calculating said correlation function and measuring said conversion efficiency of said catalyst used for said exhaust gas purification has an open-loop control period of the air fuel ratio before, after or before and after said correlation function being calculated.

14. A conversion efficiency measuring apparatus of a catalyst used for an exhaust gas purification of an internal combustion engine according to claim 4, wherein said means for calculating said correlation function and measuring said conversion efficiency of said catalyst used for said exhaust gas purification comprises a calculation means for calculating said correlation function, a memory means for memorizing the conversion efficiency estimated value of said catalyst corresponding to a period of said first rectangular wave signal as a comparison level which is used for estimating the conversion efficiency of said catalyst and a comparison means for comparing an output signal from said calculation means with an output signal from said memory means.

15. A conversion efficiency measuring apparatus of a catalyst used for an exhaust gas purification of an internal combustion engine according to claim 4, wherein said means for calculating said correlation function and measuring said conversion efficiency of said catalyst used for said exhaust gas purification comprises a calculation means for calculating said correlation function, a memory means for memorizing previously a predetermined phase difference between output signals of the upstream and downstream side exhaust gas component sensing means as a comparison level which is used for estimating the conversion efficiency o said catalyst used for said exhaust gas purification and a comparison means for discriminating whether the phase difference between an output signal of said calculation means and an output signal of said memory means reaches said predetermined phase difference.

16. A conversion efficiency measuring apparatus of a catalyst used for an exhaust gas purification of an internal combustion engine according to claim 5, wherein said means for calculating said correlation function and measuring said conversion efficiency of said catalyst used for said exhaust gas purification generates an output signal for estimating the conversion efficiency of said catalyst used for said exhaust gas purification by comparing at least one signal among an absolute value of said correlation function, a maximum value of said correlation function or a phase having the maximum value of said correlation function with a comparison level for estimating said conversion efficiency of said catalyst used for said exhaust gas purification.

17. A conversion efficiency measuring apparatus of a catalyst used for an exhaust gas purification of an internal combustion engine according to claim 5, wherein said means for calculating said correlation function and measuring said conversion efficiency of said catalyst used for said exhaust gas purification calculates said complement signal of said correlation function within an interval of integral multiples of an air fuel ratio feedback control period.

18. A conversion efficiency measuring apparatus of a catalyst used for an exhaust gas purification of an internal combustion engine according to claim 5, wherein said means for calculating said correlation function and measuring said conversion efficiency of said catalyst used said exhaust gas purification has an open-loop control period of the air fuel ratio before, after or before and after said complement signal of said correlation function being calculated.

19. A conversion efficiency measuring apparatus of a catalyst used for an exhaust gas purification of an internal combustion engine according to claim 5, wherein said means for calculating said correlation function and measuring said conversion efficiency of said catalyst used for said exhaust gas purification comprises a calculation mean for calculating a reversed value of said correlation function, a memory means for memorizing the conversion efficiency estimated value of said catalyst corresponding to a period of said first rectangular wave signal as a comparison level which is used for estimating the conversion efficiency of said catalyst used for said exhaust gas purification and a comparison means for comparing an output signal from said calculation means with an output signal from said memory means.

20. A conversion efficiency measuring apparatus of a catalyst used for an exhaust gas purification of an internal combustion engine according to claim 5, wherein said means for calculating said correlation function and estimating said conversion efficiency of said catalyst used for said exhaust gas purification comprises a calculation means for calculating a reversed value of said correlation function, a memory means for memorizing previously a predetermined phase difference between output signals of the upstream and downstream side exhaust gas component sensing means as a comparison level which is used for estimating the conversion efficiency of said catalyst used for said exhaust gas purification and a comparison means for discriminating whether the phase difference between an output signal of said calculation means and an output signal of said memory means reaches said predetermined phase difference.

21. A conversion efficiency measuring apparatus of a catalyst used for an exhaust gas purification of an internal combustion engine according to claim 8, wherein said open loop control period of said air fuel ratio control is a period more than two rotations of the engine.

22. A conversion efficiency measuring apparatus of a catalyst used for an exhaust gas purification of an internal combustion engine according to claim 10, wherein said means for calculating said correlation function and measuring said conversion efficiency of said catalyst used for said exhaust gas purification generates an output signal for estimating the conversion efficiency of said catalyst used for said exhaust gas purification by comparing at least one signal among an absolute value of said correlation function and a reversed value of said correlation function, a maximum value of said correlation function or a phase having the maximum value of said correlation function with a comparison level for estimating said conversion efficiency of said catalyst used for said exhaust gas purification.

23. A conversion efficiency measuring apparatus of a catalyst used for an internal combustion engine according to claim 10, wherein said means for calculating said correlation function and measuring said conversion efficiency of said catalyst used for said exhaust gas purification calculates said correlation function and a reversed value of said correlation function within an interval of integral multiples of an air fuel ratio feedback control period.

24. A conversion efficiency measuring apparatus of a catalyst used for an exhaust gas purification of an internal combustion engine according to claim 10, wherein said means for calculating said correlation function and measuring said conversion efficiency of said catalyst used for said exhaust gas purification has an open-loop control period of the air fuel ratio control before, after or before and after said correlation function and a reversed value of said correlation function being calculated.

25. A conversion efficiency measuring apparatus of a catalyst used for an exhaust gas purification of an internal combustion engine according to claim 10, wherein said means for calculating said correlation function and measuring said conversion efficiency of said catalyst used for said exhaust gas purification comprises a calculation means for calculating said correlation function and a reversed value of said correlation function, a memory means for memorizing previously a predetermined phase difference between output signals of the upstream and downstream side exhaust gas component sensing means as a comparison level which is used for estimating the conversion efficiency of said catalyst used for said exhaust gas purification and a comparison means for discriminating whether the phase difference between an output signal of said calculation means and an output signal of said memory means reaches said predetermined phase difference.

26. A conversion efficiency measuring apparatus of a catalyst used for an exhaust gas purification of an internal combustion engine according to claim 10, wherein said means for calculating said correlation function and measuring said conversion efficiency of said catalyst used for said exhaust gas purification comprises a calculation means for calculating said correlation function and a reversed value of said correlation function, a memory means for memorizing previously a predetermined phase difference between output signals of the upstream and downstream side exhaust gas component sensing means as a comparison level which is used for estimating the conversion efficiency of said catalyst used for said exhaust gas purification and a comparison means for discriminating whether the phase difference between an output signal of said calculation means and an output signal of said memory means reaches said predetermined phase difference.

27. A conversion efficiency measuring apparatus of a catalyst used for an exhaust gas purification of an internal combustion engine according to claim 13, wherein said open-loop control period of said air fuel ratio control is a period more than two rotations of the engine.

28. A conversion efficiency measuring apparatus of a catalyst used for an exhaust gas purification of an internal combustion engine according to claim 18, wherein said open-loop control period of said air fuel ratio control is a period more than two rotations of the engine.

29. A conversion efficiency measuring apparatus of a catalyst used for an exhaust gas purification of an internal combustion engine according to claim 21, wherein said open-loop control period of said air fuel ratio control is a period more than two rotations of the engine.

30. A conversion efficiency measuring method of a catalyst used for an exhaust gas purification of an internal combustion engine, comprising:

a step for measuring an output signal form an exhaust gas component sensing means provided at upstream and downstream sides of said catalyst used for an exhaust gas purification of an internal combustion engine, a step of calculating a correlation function based on said output signal of said exhaust gas component sensing means, a step of retrieving a comparison level which is used for estimating said conversion efficiency of said catalyst of said exhaust gas purification, and a step of measuring said conversion efficiency of said catalyst used for said exhaust gas purification by comparing an output signal of said correlation function with an output signal of said comparison level.

31. A conversion efficiency measuring method of a catalyst used for an exhaust gas purification of an internal combustion engine according to claim 30, wherein said step of calculating said correlation function calculates said correlation function based on a first rectangular wave signal which is generated by comparing an output signal from the exhaust gas component sensing means provided at said upstream side of said catalyst used for said exhaust gas purification with a first comparison level and a second rectangular wave signal which is generated by comparing another output signal from the exhaust gas component sensing means provided at said downstream side of said catalyst used for said exhaust gas purification with a second comparison level.

32. A conversion efficiency measuring method of a catalyst used for an exhaust gas purification of an internal combustion engine according to claim 31, wherein said step of calculating said correlation function has a step of calculating a complement function of said correlation function and said step of measuring said conversion efficiency of said catalyst used for said exhaust gas purification outputs a signal by comparing a signal of said complement function with an output signal of said comparison level.

33. A conversion efficiency measuring method of a catalyst used for an exhaust gas purification of an internal combustion engine according to claim 31, wherein said step of calculating said correlation function has a step of calculating said correlation function and a complement function of said correlation function and said step of estimating said conversion efficiency of said catalyst used for said gas purification outputs a signal by comparing signals of said correlation function and said complement function of said correlation function with an output signal of said comparison level.

*34. A conversion efficiency measuring apparatus of a catalyst used for an exhaust gas purification of an internal combustion engine comprising:*

*a catalyst used for an exhaust gas purification provided at an exhaust gas passage of an internal combustion engine;*

*gas component sensing means provided at an upstream side and a downstream side of said catalyst used for said exhaust gas purification;*

*means for calculating a correlation function based on an output signal from said gas component sensing means for estimating the conversion efficiency of said catalyst for said exhaust gas purification; and*

*means for comparing a calculated value of the correlation function with a comparison value.*

*35. A conversion efficiency measuring method of a catalyst used for an exhaust gas purification of an internal combustion engine comprising the steps of:*

*providing an output signal from a gas component sensing means provided at an upstream side and a downstream side of said catalyst used for an exhaust gas purification of an internal combustion engine;*

*calculating a correlation function based on said output signal from said gas component sensing means;*

*retrieving a comparison level for estimating the conversion efficiency of said catalyst of said exhaust gas purification; and*

*comparing a calculated value of the correlation function with said comparison level.*

*36. A conversion efficiency measuring apparatus according to claim 34, wherein the means for comparing includes means for indicating whether the catalyst is degraded or not.*

*37. A conversion efficiency measuring method according to claim 35, further including the step of indicating whether the catalyst is degraded or not based on the step of comparing the calculated value of the correlation function with the comparison level.*

* * * * *